US012004496B2

(12) United States Patent
Jansen et al.

(10) Patent No.: US 12,004,496 B2
(45) Date of Patent: Jun. 11, 2024

(54) INSECT TRAY WITH COVER, RACK FOR SAID TRAY, USE OF AN ASSEMBLY OF SAID RACK WITH AT LEAST ONE TRAY

(71) Applicant: Protix B.V., Dongen (NL)

(72) Inventors: Jaco Jansen, Breda (NL); Willemijn Lever, Nijmegen (NL); Raymond Joseph Leushuis, Alphen (NL)

(73) Assignee: Protix B.V., Dongen (NL)

( * ) Notice: Subject to any disclaimer, the term of this patent is extended or adjusted under 35 U.S.C. 154(b) by 755 days.

(21) Appl. No.: 16/955,054

(22) PCT Filed: Dec. 21, 2018

(86) PCT No.: PCT/NL2018/050869
§ 371 (c)(1),
(2) Date: Jun. 18, 2020

(87) PCT Pub. No.: WO2019/125164
PCT Pub. Date: Jun. 27, 2019

(65) Prior Publication Data
US 2021/0000090 A1 Jan. 7, 2021

(30) Foreign Application Priority Data

Dec. 22, 2017 (NL) ...................................... 2020155

(51) Int. Cl.
*A01K 67/033* (2006.01)
(52) U.S. Cl.
CPC .................................. *A01K 67/033* (2013.01)
(58) Field of Classification Search
CPC ..................................................... A01K 67/033
See application file for complete search history.

(56) References Cited

U.S. PATENT DOCUMENTS 2,896,374 A * 7/1959 Perin ...................... A01G 31/06
47/62 R
3,006,106 A * 10/1961 Shuler .................... A01K 97/04
43/4
(Continued)

FOREIGN PATENT DOCUMENTS

CA 2 399 521 A1 2/2004
CN 106212387 A * 12/2016
(Continued)

OTHER PUBLICATIONS

Shandan, "Cultivation and utilization of medicinal insects", pp. 70-71, Guangxi Science and Technology Press, Jan. 2006.

*Primary Examiner* — Morgan T Jordan
(74) *Attorney, Agent, or Firm* — N.V. Nederlandsch Octrooibureau (57) ABSTRACT

The invention relates to a tray for use in large-scale industrial insect farming. More in particular, the invention relates to a live insects tray for incubating insects prepupae and pupae, the tray having a space limited by walls, for housing insect prepupae and pupae, wherein the walls are impenetrable by an insect, and that at least one of the walls is at least partly permeable for gases, such as the top wall. Furthermore, the invention relates to a rack for holding at least one tray and relates to an assembly having said rack and at least one of said trays. The invention also relates to the use of said rack with at least one tray or said assembly for incubating insect prepupae. In addition the invention relates to a method for incubating insect prepupae and/or insect pupae, preferably of black soldier fly.

16 Claims, 5 Drawing Sheets

(56) References Cited

U.S. PATENT DOCUMENTS

| | | | | |
|---|---|---|---|---|
| 3,345,974 A * | 10/1967 | Phillips | A01K 67/033 | 119/51.01 |
| 3,468,289 A * | 9/1969 | Broida | B65D 81/266 | 119/6.5 |
| 3,580,219 A * | 5/1971 | Stebbins | A01K 67/033 | 119/6.5 |
| 3,874,335 A * | 4/1975 | Galasso | A01K 63/003 | 119/6.5 |
| 3,946,780 A * | 3/1976 | Sellers | B65D 51/1616 | 426/8 |
| 4,100,023 A * | 7/1978 | McDonald | C02F 3/28 | 435/813 |
| 4,212,267 A * | 7/1980 | Patterson | A01K 1/031 | 119/6.5 |
| 4,252,080 A * | 2/1981 | Gioia | A01K 67/033 | 119/6.5 |
| 4,365,372 A * | 12/1982 | Norman | A01K 67/033 | 449/4 |
| 4,411,220 A * | 10/1983 | Voegele | A01K 67/033 | 119/6.6 |
| 4,498,420 A * | 2/1985 | Botterman | A01K 67/033 | 119/6.5 |
| 4,646,683 A * | 3/1987 | Maedgen, Jr. | A01K 67/033 | 119/6.5 |
| 4,785,764 A * | 11/1988 | Muller | A01K 67/033 | 119/6.5 |
| 4,797,367 A * | 1/1989 | Pinder | C05F 17/907 | 435/290.1 |
| 4,924,810 A * | 5/1990 | Tominaga | A01K 1/03 | 119/6.5 |
| 4,968,624 A * | 11/1990 | Bacehowski | B65D 77/065 | 206/524.2 |
| 5,074,247 A * | 12/1991 | Gupta | A01K 1/031 | 119/6.5 |
| 5,178,094 A * | 1/1993 | Carr | A01K 67/033 | 119/6.5 |
| 5,351,643 A * | 10/1994 | Hughes | A01K 67/033 | 119/6.5 |
| 5,554,533 A * | 9/1996 | Bedding | A01K 67/033 | 422/562 |
| 5,611,172 A * | 3/1997 | Dugan | A01G 7/00 | 47/1.01 R |
| 5,630,374 A * | 5/1997 | Cunningham | A01K 97/04 | 119/6.5 |
| 5,784,991 A * | 7/1998 | Ukishiro | A01K 67/033 | 119/6.5 |
| 5,819,685 A * | 10/1998 | Kappelt | A01K 67/033 | 119/6.5 |
| 5,895,310 A * | 4/1999 | Otomo | A01K 67/033 | 449/20 |
| 5,927,230 A * | 7/1999 | Frank | C07K 14/4359 | 119/6.5 |
| 6,105,535 A * | 8/2000 | Atamian | A01K 67/033 | 119/6.5 |
| 6,129,051 A * | 10/2000 | Jessie | A01K 31/06 | 220/9.4 |
| 6,130,084 A * | 10/2000 | Endencia | A01K 67/033 | 435/308.1 |
| 6,244,213 B1 * | 6/2001 | Tedders | A01K 67/033 | 119/6.6 |
| 6,561,125 B1 * | 5/2003 | Lohsomboon | A01K 67/033 | 119/6.5 |
| 7,086,924 B2 * | 8/2006 | Mills | A01K 67/033 | 119/6.5 |
| 7,923,249 B2 * | 4/2011 | Rise | A01C 1/02 | 435/430 |
| 8,544,416 B2 * | 10/2013 | Gabriel | A01K 1/031 | 119/455 |
| 10,051,845 B1 * | 8/2018 | Massaro | A01K 29/005 | |
| 10,123,940 B2 * | 11/2018 | Pavlik | F25D 31/00 | |
| 10,159,229 B2 * | 12/2018 | Marchant | F21V 7/22 | |
| 10,589,197 B2 * | 3/2020 | Rhodes | C12M 33/14 | |
| 2002/0009803 A1 * | 1/2002 | Vajta | C12M 21/06 | 435/325 |
| 2004/0020976 A1 * | 2/2004 | Jochens | A01K 1/0245 | 229/178 |
| 2004/0211368 A1 * | 10/2004 | Chen | A01K 1/0052 | 119/455 |
| 2005/0120963 A1 * | 6/2005 | Vadis | A01K 63/003 | 119/6.5 |
| 2006/0266292 A1 * | 11/2006 | Duckworth | A01K 1/0245 | 119/6.5 |
| 2008/0047492 A1 * | 2/2008 | Vadis | A01K 67/033 | 119/6.5 |
| 2008/0078328 A1 * | 4/2008 | Orup | A01K 63/006 | 119/51.01 |
| 2009/0223116 A1 * | 9/2009 | Meghji | A01M 1/026 | 43/118 |
| 2010/0050946 A1 * | 3/2010 | Tsyrlin | A01K 67/033 | 119/6.5 |
| 2011/0314562 A1 * | 12/2011 | Lu | A01K 67/033 | 119/6.5 |
| 2013/0340338 A1 * | 12/2013 | Lin | A01G 31/02 | 47/62 R |
| 2014/0020630 A1 * | 1/2014 | Courtright | A01K 29/00 | 119/6.6 |
| 2014/0295733 A1 * | 10/2014 | Waite | A01K 49/00 | 449/13 |
| 2015/0122182 A1 * | 5/2015 | Aldana | A01K 67/033 | 119/6.6 |
| 2015/0223496 A1 * | 8/2015 | Kitazumi | A01K 67/033 | 119/6.5 |
| 2017/0360014 A1 * | 12/2017 | Hall | B65G 1/0492 | |
| 2018/0070565 A1 * | 3/2018 | Massaro | A01K 67/033 | |
| 2021/0000090 A1 * | 1/2021 | Jansen | B33Y 80/00 | |

FOREIGN PATENT DOCUMENTS

| | | | | |
|---|---|---|---|---|
| CN | 106719453 A | * | 5/2017 | |
| DE | 20 2008 003 950 U1 | | 7/2008 | |
| DE | 202015001045 U1 | * | 9/2015 | A01K 1/03 |
| EP | 0144994 A2 | * | 6/1985 | |
| EP | 204999 A | * | 12/1986 | A01K 67/033 |
| EP | 2792237 A1 | * | 10/2014 | A01K 67/033 |
| GB | 2110516 A | * | 6/1983 | A01K 67/0332 |
| GB | 2479004 A | * | 9/2011 | A01K 1/03 |
| KR | 20090055138 A | * | 6/2009 | |
| KR | 20090116586 A | * | 6/2009 | |
| KR | 20110067253 A | * | 6/2011 | |
| KR | 20120000770 U | * | 2/2012 | |
| KR | 20120000771 U | * | 2/2012 | |
| KR | 20140036387 A | * | 3/2014 | |
| KR | 2015033025 A | * | 4/2015 | A01G 9/02 |
| KR | 20150056333 A | * | 5/2015 | |
| KR | 20160027725 A | * | 3/2016 | |
| KR | 20170022170 A | * | 3/2017 | |
| WO | WO-2006054108 A1 | * | 5/2006 | A01K 67/033 |
| WO | WO-2013166590 A1 | * | 11/2013 | A01K 67/033 |
| WO | 2015/023178 A1 | | 2/2015 | |

* cited by examiner

INSECT TRAY WITH COVER, RACK FOR SAID TRAY, USE OF AN ASSEMBLY OF SAID RACK WITH AT LEAST ONE TRAY

TECHNOLOGICAL FIELD

The invention relates to a tray for use in large-scale industrial insect farming. More in particular, the invention relates to a live insects tray for incubating insects prepupae and pupae, the tray comprising a space limited by walls, for housing insect prepupae and pupae, wherein the walls are impenetrable by an insect, characterized in that at least one of the walls, such as the op wall, is at least partly permeable for gases. The tray comprises a side wall provided with a closable opening, for loading and unloading the tray with (pre)pupae. The tray is for example a bottle or flask, such as a bottle made of a polymer material. Furthermore, the invention relates to a rack for holding at least one tray and relates to an assembly comprising said rack and at least one of said trays. The invention also relates to the use of said rack with at least one tray or said assembly for incubating insect prepupae. In addition the invention relates to a method for incubating insect prepupae and/or insect pupae, preferably of black soldier fly.

BACKGROUND

Insects are considered one of the most promising means for protein and for organic residual recovery. Prominent examples of species proposed for the indicated applications include the black soldier fly (*Hermetia illucens*), the house fly (*Musca domestica*), and the mealworm (*Tenebrio molitor* L.).

Methods improving the efficiency of insect farming relating to improvements in farming hygiene and improvements in required space and volume of a farm demanded by the desired large-scale production of insect-based materials, are particularly valuable for large scale production. This, amongst others because of the working temperature for the various steps in the process of providing insect-based products, which is above ambient temperature and therewith causing a risk for accelerated growth of any contaminating microbe present at any location in the insect-based material production cycle. In addition, since insect farming which is economically feasible requires relatively large scale farming facilities, i.e. farms, any reduction in the required floor area and/or size and volume of any of the farming equipment, farming tools, farm house, barns, cages, etc., contributes to cost savings and reduced environmental impact and therewith to improved added value per unit of insect-based material produced on the farm. Ideally, enlarging insect farming facilities relating to any and each aspect of farming goes hand in hand with reducing the size (and numbers) of any and all equipment, machinery, devices, disposables, etc., used and involved in said large scale insect farming.

Up till now, economics of scale with regard to insect farming is only applicable in theory, since for many, if not all, of the steps and activities involved in insect farming that would be economically feasible, suitable machinery, equipment, farming facilities, etc., with regard to reduced risk for contaminating the environment and with regard to optimal size reductions are not available to the required extent. Thus, methods and means for efficacious and beneficial insect farming at industrial-scale, are at present not available in the art.

SUMMARY

It is a first goal of the present invention to take away the above mentioned disadvantages, or at least to provide a useful alternative to the state of the art.

It is an object of the current invention to provide tools and equipment for farming of insects such as prepupae and pupae, which tools and equipment have reduced size and volume.

It is an object of the current invention to provide a means for farming insects, preferably prepupae and/or pupae, which bears reduced risk for contaminating the environment of the farming facilities and the farming tools and equipment with insects.

It is another or alternative object to provide a means for improved and efficient transport of live insects such as live neonate larvae from the location where the insects hatch to a location where the live insects are countable and preferably dosable and/or analyzable with regard to the age of the live insects transported by using the means for automated and efficient transport of live insects.

Furthermore, it is yet another or alternative object to incubate insect prepupae and/or insect larvae, such as those of black soldier fly, at least in one of: an incubation chamber such as a tray with a reduced size and volume than currently available; and/or an incubation chamber such as a tray which introduces less risk for contaminating the environment of the incubation chamber with live insects such as prematurely emerged adult insects from the pupae.

At least one of the above objectives is achieved by a tray for incubating prepupae and/or pupae, comprising a space limited by walls, for housing insect prepupae and pupae, such as those from black soldier fly, wherein the walls are impenetrable by an insect, e.g. an adult insect and/or a prepupae, characterized in that at least one of the walls of the tray is at least partly permeable for gases.

The objective of down-scaling the size and/or volume of insect incubating equipment and/or tools and/or housing such as cages and trays, and/or the objective of preventing the insect housing environment from contamination with insects present in said insect housing, is achieved by application of the tray for incubating pupae, comprising a space limited by walls, for housing insect prepupae and pupae, wherein the walls are impenetrable by an insect, characterized in that at least one of the walls is at least partly permeable for gases of the invention. That is to say, the inventors established that the height of the tray commonly in use for incubating insect prepupae and insect pupae could be reduced with at least 25%, such as to a height of 5 cm-12 cm, such as about 8 cm, without losing any farming efficiency with regard to the yield of adult insects from the incubated pupae, and concomitant with the prevention of any contamination of the environment of the insect incubation gear with insects, more in particular contamination with insect prepupae and/or adult insects was fully prevented, when applying the tray of the invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under, front, back, and the like in the description and the claims are used for descriptive purposes and not necessarily for describing relative positions. The terms so used are interchangeable under appropriate circumstances and the embodiments of the invention described herein can operate in other orientations than described or illustrated herein.

The embodiments of the invention described herein can operate in combination and cooperation, unless specified otherwise.

Furthermore, the various embodiments, although referred to as "preferred", "preferably", or "e.g." or "for example" or "in particular", "particularly", are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of for example the expression "an assembly comprising A and B" should not be limited to assemblies consisting only of components A and B, rather with respect to the present invention, the only enumerated components of the assembly are A and B, and further the claim should be interpreted as including equivalents of those components.

A first aspect of the current invention relates to a tray for incubating pupae, comprising a space limited by walls, for housing insect prepupae and pupae, wherein the walls are impenetrable by an insect, characterized in that at least one of the walls is at least partly permeable for gases. In particular, the walls of the tray of the invention are impermeable for insect prepupae and for adult insects, such as prepupae and adult insects of black soldier fly. In particular, the tray of the invention is impermeable for insects in the direction from the inside of the tray outwardly. One or more of the walls of the tray of the invention are at least in part transparent or semi-transparent for light such as daylight or light from an artificial source, in one embodiment of the invention. For example, at least a portion of one or more of the side walls of the tray of the invention is/are at least semi-transparent for light, in one embodiment of the invention.

For example, the tray for incubating pupae comprises a space limited by walls, for housing insect prepupae and pupae,
  wherein said walls comprise a first side wall, a second side wall, a third side wall, a fourth side wall, a bottom wall and a top wall
    and said walls are impenetrable by an insect
    and the first side wall comprises an openable part,
  wherein the top wall is at least partly permeable for gases,
  characterized in that the tray is a bottle and the openable part in the first side wall is a closable opening in a bottle neck, and in that the height of the four side walls of the tray is between 2.2 cm and 40 cm. Typically, the height is between 2.2 cm and 8 cm, or between 2.3 cm and 5 cm, or about 8 cm. For example, the top wall is comprising a mesh made of polypropylene, with openings, the openings for example having a surface of about 4 mm$^2$ to 12 mm$^2$, such as about 8 mm$^2$. Typically, the openings are circular or ellipsoid or squaric openings. For example, the side walls, bottom wall and/or top wall are made of a polymer material such as a polymer blend or polypropylene. Typically, the tray is a bottle with an inner bottom wall surface area of 16 cm-40 cm times 20 cm-60 cm, or of 20 cm-30 cm times 30 cm-50 cm.

In one embodiment, the tray according to the invention has walls, wherein said walls limiting the space of the tray comprise side walls, a bottom wall and a top wall, and wherein the at least one wall of the tray that is at least partly permeable for gases according to the invention, is the top wall of the tray and/or is at least one of the side walls of the tray. In one embodiment, the tray according to the invention has walls, wherein the top wall is the at least one wall of the tray that is at least partly permeable for gases according to the invention. In one embodiment, the tray according to the invention has walls, wherein two side walls located opposite to each other provide for the at least one wall of the tray that is at least partly permeable for gases according to the invention, although a tray having a top wall which is at least partly permeable for gases is preferred.

In one embodiment, the tray according to the invention comprises walls, wherein the at least one wall of the tray that is at least partly permeable for gases, is permeable for at least water vapor, oxygen and carbon dioxide. Preferred is the tray wherein the top wall is permeable for at least water vapor, oxygen and carbon dioxide. Preferably, the at least one wall of the tray that is at least partly permeable for gases, for example the top wall, is permeable for at least air such as ambient air and for water vapor, preferably at temperatures of between 0° C. and 40° C., more preferably between 4° C. and 37° C., most preferably between 14° C. and 28° C., such as for example at temperatures of about 2° C., 8° C., 11° C., 16° C., 20° C., 23° C., 26° C., 32° C. or 35° C., according to the invention. It is preferred that the at least one wall of the tray that is at least partly permeable for gases, e.g. the top wall, is at least permeable for gases such as air and ammonia and water vapor in the direction from inside the tray of the invention outwardly when at least carbon dioxide and water vapor and ammonia are considered, and in the direction from the environment surrounding a tray of the invention inwardly into the tray when at least oxygen is considered. In particular, at least one wall of the tray that is at least partly permeable for gases, such as the top wall, is permeable for air enriched in one or more gases selected from oxygen and carbon dioxide, and is permeable for air comprising at least ammonia, and is permeable for air having a relative humidity of at least 30%, such as a relative humidity of between 40% and 100%, preferably between 50% and 100%, such as for example 60%, 70%, 80% or 90%, according to the invention. Preferably, the top wall is permeable for at least water vapor, oxygen and carbon dioxide, and in addition, permeable for ammonia.

In one embodiment, the tray according to the invention comprises walls, wherein the at least one wall of the tray that is at least partly permeable for gases, for example the top wall, is further permeable for at least ammonia. In one embodiment, the tray according to the invention comprises walls, wherein the at least one wall of the tray that is at least partly permeable for gases is the top wall of the tray, and wherein said top wall is at least permeable for water vapor, carbon dioxide and water vapor in the direction from the inside of the tray outwardly to the environment surrounding said tray, and at least permeable for oxygen in the direction from the outside of the tray, i.e. the air surrounding the tray, inwardly towards the interior of the tray, according to the invention. It is part of the invention that the permeability of the at least one wall of the tray that is at least partly permeable for gases for gases, such as the top wall, is such that incubating insect pupae in the tray of the invention is evenly efficacious and efficient when compared to incubating the insect pupae in a tray wherein the at least one wall of the tray that is at least partly permeable for gases is omitted, such that such a tray has at least one side of the tray which is exposed to the environment. Such trays having e.g. an open top side without a wall covering said top side are commonly in use for farming insects at small scale. A drawback of such open-topped trays for incubating insect pupae of the state of the art is amongst others that the environment is continuously exposed to the insect pupae. Due to age differences between individual pupae in a colony of pupae in such open-topped tray, as the time goes by the risk for more and more adult insects emerging first from the oldest pupae contaminating the surrounding environment of said open-topped tray increases. In fact, emergence of at least some adult insects and escape into the environment can hardly be prevented when using currently available pupae incubation trays. It is now due to the current inventors that a solution to this problem has become available. Furthermore, covering at least in part (pre)pupae inside the tray with for example the top wall, contributes to prevention of contamination of the (prep)pupae with contaminants present in the exterior surrounding of the tray that could otherwise enter the tray when the tray would have a completely open top side.

In one embodiment, the tray according to the invention comprises walls, wherein the at least one wall of the tray that is at least partly permeable for gases, such as the top wall, is made of a material selected from a metal such as aluminum, an alloy such as stainless steel, a polymer, a polymer blend, and a plastic such as a blow-molded polymer, a blow-molded polymer blend or a blow-molded plastic, or a combination thereof. According to the invention, the at least one wall of the tray that is at least partly permeable for gases preferably is made of a polymer or a polymer blend such as a blow-molded polymer or a blow-molded polymer blend. An example is the tray, wherein the top wall is permeable at least in part for gases and is made of a polymer or a polymer blend, such as blow-molded polymer (blend). Furthermore, for example the side walls and the bottom wall are made of a polymer or a polymer blend, that is for example blow-molded. Typically, the side walls and the bottom wall have a thickness of 0.5 mm-6 mm, such as about 3 mm. Typically, the top wall has a similar thickness of 1.5 mm-6 mm, such as about 1.7 mm.

In one embodiment, the tray according the invention comprises walls, wherein the at least one wall of the tray that is at least partly permeable for gases, for example the top wall, is made of a polymer or a polymer blend that allows passage of at least water vapor, oxygen and carbon dioxide. Preferably, the wall of the tray that is at least partly permeable for gases, for example the top wall, is in addition also permeable for ammonia. Beneficially incubating insect pupae up to a stage that adult insects can emerge requires supply of fresh air comprising sufficient oxygen to a batch of pupae incubated in the tray of the invention. The oxygen is thus provided as part of the air passing the at least one wall of the tray that is at least partly permeable for gases, for example the top wall, from the environment of the tray inwardly towards the pupae residing at the surface of the bottom wall of the tray, according to the invention. Typically, the air invading the interior of the tray through the at least one wall of the tray that is at least partly permeable for gases, for example the top wall, has ambient temperature, i.e. between 18° C. and 22° C., or has a temperature of between 12° C. and 37° C., such as for example between 20° C. and 30° C., or about 16° C. or about 24° C., or any selected temperature or average temperature falling within this range according to the invention. Preferably, the relative humidity of the gas comprising oxygen, such as air, which is passing the at least one wall of the tray that is at least partly permeable for gases from outside inwardly into the tray, is between about 30% and 60%, preferably about 40% to 50%, according to the invention. Prepupae present in the tray and allowed to transfer into pupae, and pupae incubated in the tray of the invention are incubated most efficiently when the air surrounding the prepupae and pupae is not too dry and not to moist, i.e. the relative air humidity is preferably not lower than about 30% and preferably not higher than about 60%. For example, the relative air humidity of the air surrounding the tray of the invention is 28%-64%, for example 30%-60%, or 35%-50%, such as 40%-45%. Therefore, it is part of the invention that applying the tray comprising at least one wall, for example the top wall, that is at least partly permeable for gases including oxygen, carbon dioxide and water vapor for incubating pupae, allows for efficient and adequate release of moisture and water vapor from the location surrounding incubated pupae towards the environment surrounding the tray. In addition, the tray of the invention allows for sufficient and adequate disposal of any carbon dioxide exceeding normal levels of carbon dioxide in ambient air, according to the invention. Pupae that are incubated in a tray produce carbon dioxide and water vapor and consume oxygen. The closed tray of the invention allows for transfer of these gases inside out the tray and vice versa such that pupae are constantly in an environment of air with optimal oxygen content, optimal carbon dioxide content and optimal water vapor content which is not too low inducing the risk for drying out of the pupae to some extent and not too high for inducing the risk of e.g. uncontrollable temperature rise in the batch of pupae.

In one embodiment, the tray according the invention comprises walls, wherein the surface of the wall that is at least partly permeable for gases, such as the top wall, is a smooth surface, such as the surface of a wall made of polished aluminum, blow-molded blend of two or more polymers, polypropylene or polished stainless steel. For example, the top wall is made of a polymer or a polymer blend. In one embodiment, the tray according the invention comprises walls, wherein the surface of the wall that is at least partly permeable for gases, for example the top wall, is a smooth surface made of polypropylene. A smooth surface in the context of the invention refers to the surface of a wall of the tray of the invention being free of ridges, protrusions, recesses, etc., wherein the wall of the tray is for example preferably polished or the like in order to provide for a surface which minimally provides any support for insect prepupae attempting to climb any wall other than crawling along the bottom wall of the tray, according to the invention. In trays currently used for insect farming, i.e. trays for incubating prepupae and/or pupae, side walls have to be at least 10 cm high, measured from the bottom wall surface of the tray to the top side of the lowest side wall of such tray of the state of the art. This height of 10 cm or more is required since prepupae searching for a place to transform into pupae are crawling throughout the tray and are climbing on top of each other once corners and side walls are reached. This causes the problem that prepupae escape from pupae incubation trays comprising side walls with a height of less than 10 cm. In order to prevent contamination of the environment of the trays by prepupae, subsequent pupae formed once escaped from a tray, and finally adult insects, currently trays with a depth of even over 10 cm are commonly in use. Such trays of the current art have commonly an open top side, i.e. (pre)pupae are exposed to the environment and not covered or shielded from contact with the surrounding. This causes at least two major drawbacks coming with current low-tech insect farming techniques. First, trays having side walls with a height of 10 cm or even larger demand a room for farming insects that is relatively large, when the incubation of pupae is scaled up with regard to the numbers of pupae required per time unit in order to achieve insect farming at economically beneficial scale. Second, scaling up current low-tech pupae incubation using the relatively large trays with relatively extended side walls, demand a relatively high amount of material for providing sufficient numbers of trays. Trays of the invention have side walls with a smallest height of less than 10 cm, such as 2 cm-9 cm, 2.1 cm-8 cm, 2.2 cm-7 cm, 2.3 cm-6 cm, 2.4 cm-5 cm, 2.5 cm-5 cm, 3 cm-4 cm, and typically the height of the side walls is 205 cm at least, such as about 8 cm. Therewith, preventing prepupae from crawling on top of each other and thereby escaping the tray.

In one embodiment, the tray according the invention comprises walls, which walls have a wall thickness of between 1 mm and 12 mm. For example, the side walls, and/or the bottom wall and/or the top wall have a thickness of 2 mm-5 mm, typically 2.5 mm-3.5 mm, such as about 3 mm. The portion of the top wall that is at least in part permeable for gases typically has a thickness of 1.2 mm-2.5 mm, such as about 1.7 mm. In one embodiment, the tray according the invention comprises walls, wherein at least one of the walls has a wall thickness of between 1 mm and 12 mm, preferably at least one of the side walls, more preferably two or all of the side walls, according to the invention. Preferably, the wall thickness of the walls of the tray of the invention is between about 3 mm and 9 mm, such as about 4 mm, 5 mm, 6 mm, 7 mm, 8 mm, or any wall thickness therein between, according to the invention. In one embodiment, the tray according the invention comprises walls, wherein at least one of the walls, preferably between two and all of the walls, such as the bottom wall and the side walls, has/have a wall thickness of between 0.6 mm and 10 mm, such as about 3 mm, wherein the wall is preferably made of polypropylene, and wherein said wall is preferably made of a polymer which is blow molded, according to the invention. In one embodiment, the tray according the invention comprises a wall, which wall has a wall thickness of between about 1.5 mm and about 10 mm, preferably with an average wall thickness of about 2.5 mm, or about 3 mm, wherein the wall is preferably made of polypropylene, and wherein said wall is preferably made of a polymer which is blow molded, according to the invention. With walls of the tray of the invention having a thickness within these ranges, for example on average about 2.5 mm polypropylene, preferably blow molded polypropylene, the temperature of the environment surrounding the trays of the invention determines the temperature inside the tray, according to the invention. Walls with these indicated thickness allow for efficient and adequate heat transfer between the air outside the tray and the content of the tray, i.e. the prepupae and/or the pupae. This way, the temperature inside the tray is temperature controlled by the temperature outside the tray. Of course, temperature control inside the tray by the air temperature outside the tray is already facilitated by the air exchange through the wall of the tray that is at least partly permeable for gases, for example the top wall, according to the invention. Excess heat produced in the incubated prepupae and/or pupae is transferred outwardly out of the tray, and the warm air outside the tray controls the desired incubation temperature inside the tray.

Preferably, all walls of the tray of the invention have a smooth surface such as the surface of walls made of polished aluminum, blow-molded blend of two or more polymers, polypropylene or polished stainless steel. In one embodiment, the tray according the invention comprises walls, wherein the surface of all walls building up the tray of the invention are made of polypropylene having a smooth surface.

In one embodiment, the tray according the invention comprises walls, wherein the at least one wall of the tray that is at least partly permeable for gases, for example the top wall, is made of polypropylene.

In one embodiment, the tray according the invention comprises walls, wherein the at least one wall of the tray that is at least partly permeable for gases, such as the top wall, is selected from a net, a gauze, a screen, a mesh, a plate provided with perforations, a membrane, a sieve and a filter. Alternatively, the at least one wall of the tray that is at least partly permeable for gases of the tray of the invention, preferably the top wall, is a membrane. For example, the wall of the tray that is at least partly permeable for gases is the top wall, wherein the top wall comprises a mesh. The mesh is for example a polypropylene mesh, such as a mesh with a thickness of about 1.7 mm and weighing about 500 gr/m$^2$. For example, such a polypropylene mesh or a mesh manufactured with a different polymer or polymer blend, has mesh openings of between 5 mm$^2$ and 10 mm$^2$, such as about 7.5 mm$^2$. An example of a mesh comprised by the top wall of the tray is a polypropylene mesh with openings of about 2.8 mm×2.8 mm, or between 2.3 mm×2.3 mm and 3.5 mm×3.5 mm. Of course, the openings of the mesh can have a rectangular shape, an ellipsoid shape, a circular shape, a triangular shape, a squaric shape, etc. The openings of the mesh have a selected size allowing sufficient and efficient transfer of gases, air, water vapour, and at the same time preventing prepupae and pupae and adult insects from transferring through the openings (at least from the interior outwardly). An example of a suitable mesh material is polypropylene mesh having openings of 2.8 mm×2.8 mm, a thickness of 1.7 mm and a surface mass of 500 gr/m$^2$, such as PP5205 (Top7even, Haarlem, The Netherlands).

In one embodiment, the tray according to the invention comprises at least one wall that is at least partly permeable for gases, for example the top wall, wherein a fraction or portion of an extended surface of the at least one wall of the tray that is at least partly permeable for gases, is at least partly permeable for gases, or wherein the whole surface area of said extended surface of the at least one wall of the tray that is at least partly permeable for gases is permeable for gases.

In one embodiment, the tray according to the invention comprises at least one wall that is at least partly permeable for gases, such as the top wall, wherein the at least one wall of the tray that is at least partly permeable for gases is at least partly permeable for air and/or ammonia.

In one embodiment, the tray according to the invention comprises at least one wall that is at least partly permeable for gases, for example the top wall, wherein the at least one wall of the tray that is at least partly permeable for gases comprises an openable part.

In one embodiment, the tray according to the invention comprises at least one wall that is at least partly permeable for gases, such as the top wall, wherein the at least one wall of the tray that is at least partly permeable for gases is a wall comprising openings selected from a screen, a mesh, a gauze, a web, a net and a plate, the plate preferably made of polypropylene, polyethylene, aluminum or stainless steel provided with perforations.

In one embodiment, the tray according to the invention comprises at least one wall that is at least partly permeable for gases, wherein the at least one wall of the tray that is at least partly permeable for gases, is a mesh, preferably made of polypropylene. For example, the at least one wall that is at least partly permeable for gases is the top wall, and for example, said top wall is comprising a mesh made of polypropylene.

In one embodiment, the tray according to the invention comprises at least one wall that is at least partly permeable for gases, for example the top wall, wherein the at least one wall of the tray that is at least partly permeable for gases, is a plate provided with one or more slits, said slits having a minor axis of between 0.7 mm and 3.8 mm, preferably between 1.0 mm and 3.5 mm, more preferably about 3.0 mm, and preferably the whole surface area of said at least one wall of the tray that is at least partly permeable for gases is provided with evenly spaced slits.

In one embodiment, the tray according to the invention comprises at least one wall that is at least partly permeable for gases, wherein the at least one wall of the tray that is at least partly permeable for gases, such as the top wall, is a screen containing circular openings, such as evenly spaced openings, said circular openings having a diameter of between 0.7 mm and 3.8 mm, preferably between 1.0 mm and 3.5 mm, more preferably about 3.0 mm, the screen preferably made of polypropylene.

In one embodiment, the tray according to the invention comprises at least one wall that is at least partly permeable for gases, for example the top wall, wherein the openings in said at least one wall that is at least partly permeable for gases allow the passage of oxygen, carbon dioxide and water vapor and wherein the form and size of said openings is such that passage of an insect, preferably a prepupae and an adult insect, preferably of a black soldier fly, through said openings is prevented.

In one embodiment, the tray according to the invention comprises at least one wall that is at least partly permeable for gases, for example the top wall, wherein the openings in said at least one wall that is at least partly permeable for gases have a circular form with a diameter of between 0.7 mm and 3.8 mm, preferably between 1.0 mm and 3.5 mm, more preferably about 3.0 mm, or an ellipse form with a minor axis with a length of between 0.7 mm and 3.8 mm and with a major axis with a length of between 0.7 mm and 3.8 mm, preferably the minor axis and the major axis of the ellipse are between 1.0 mm and 3.5 mm, more preferably both axis are about 3.0 mm. For example, these openings have a squaric form with sides of 2.8 mm. It has been established by the inventors that openings of these indicated sizes are adequate and sufficient in preventing crawling prepupae from escaping the interior of the tray of the invention once supplied to the tray, that such openings adequately prevent adult insects from escaping the tray once emerged from incubated pupae, and that openings of these sizes efficaciously allow the passage of gas such as air comprising water vapor and/or ammonia from outside the tray inwardly and vice versa, thereby contributing to efficient pupae incubation to the benefit of insect farming at desired large scale, i.e. fruitful industrial scale, according to the invention. Furthermore, the inventors not only established that a wall such as the top wall of the tray of the invention provided with openings within these size limitations contributes to efficient and adequate exchange of water vapor and gases in the desired inside-out direction or outside-in direction, while at the same time keeping insects inside the tray, though also established that the tray according to the invention comprising at least one wall that is at least partly permeable for gases, such as the top wall, wherein the openings in said permeable wall have the above outlined size range, has a top wall at which condensation of water vapor is prevented, according to the invention. A top wall provided with the openings having a size range as indicated does not become occupied by water droplets at the major surface of said wall located at the interior side of the tray, according to the invention. Water vapor is sufficiently transferred from the interior of the tray outwardly to the environment, such that condensation at the inner side of the major surfaces of the walls of the tray does not occur. This way, contacting prepupae and pupae during incubation in the tray of the invention with liquid water is thus prevented, therewith avoiding negative influences of said liquid water on the progress and efficiency of the transformation to pupae and subsequently adult insects, and on the health of the insects. Furthermore, the tray with at least one wall of the tray that is at least partly permeable for gases, for example the top wall, said wall comprising openings with a size of the aforementioned dimension(s), allow for efficient and efficacious heat transfer inside the tray outwardly and outside the tray inwardly. This way, the top-covered tray prevents at least in part entrance of contaminants into the tray, while allowing efficient temperature control inside the tray. Excess heat produced by the (pre)pupae is transferred outwardly from the interior of the tray to the surrounding, and (pre)pupae inside the tray are kept at a constant temperature by constant temperature equalization based on temperature controlled air entering the tray through the wall of the tray that is at least partly permeable for gases, for example the top wall.

In one embodiment, the tray according to the invention comprises walls, wherein said walls of the tray, including the at least one wall of the tray that is at least partly permeable for gases, such as the top wall, are impenetrable for adult insects such as black soldier flies. Herewith, insects are prevented from escaping the tray, and insects can not enter the tray.

In one embodiment, the tray according to the invention comprises walls, wherein the at least one wall of the tray that is at least partly permeable for gases, for example the top wall, is made of the same material as the further walls of said tray, preferably made of polypropylene. Trays produced form a single type of material provide for simple ways to connect for example walls of the tray, for example by welding, gluing, etc., i.e. any methods of attaching for example polypropylene parts together known in the art, which is preferable for fast and easy production of series of trays.

In one embodiment, the tray according to the invention comprises side walls, wherein at least one side wall of said tray comprises an openable part. The openable part is for example comprised by the first side wall. Such an opening is desired, especially when the tray is produced as one part, for allowing loading a batch of prepupae in the tray, for allowing harvesting a batch of incubated pupae out of the tray, etc. Such an opening is for example centrally positioned in a side wall of the tray, or is for example positioned off-center, such as at or near a side of the side wall comprising the opening. Off-center positioning of the opening facilitates fast and easy pouring of pupae out of the tray, for example. The opening is for example a circular or ellipsoid or rectangular or squaric opening with dimensions of 6 cm-13 cm, such as about 7 cm, about 8 cm, about 9 cm.

In one embodiment, the tray according to the invention has an openable part, wherein the openable part has a circular cross section with a diameter of between 4 cm and 14 cm or a rectangular cross section with sides of between 4 cm and 14 cm. Openings this size allow for fast and convenient entrance of a prepupae batch into the interior of the tray and allow for easy and fast release of incubated pupae out of the tray, once pupae are at the end of the pupae incubation phase. The opening of the openable part in a side wall of the tray is for example located off-center in the side wall. The off-center located opening allows for fast and easy pouring of the content of the tray, wherein pupae exit the tray in minimal time when the tray is tilted and by minimally tilting the tray for efficient and complete release of the content of the tray. The opening is for example located in the first side wall.

In one embodiment, the tray according to the invention is a bottle and the openable part is a closable opening in the bottle neck, preferably a bottle neck provided with a screw thread configured for receiving a screw cap for closing the tray. For example, the bottle, or flask, is provided with a bottle neck provided with a screw thread provided with a bayonet catch. Such a bayonet catch provides the advantage that the bottle neck air-tight receives a screw cap by about 90° rotating the screw cap on the screw thread. This way, the required time and force and amount of movement and handling required from the operator who closes or opens the bottle is minimal, while the bottle is sufficiently closed. Opening the bottle in turn again requires minimal force, time and movement, since the screw cap is released from the screw thread by a 90° turn.

The tray, for example a bottle, or flask, is in embodiments provided with one or more ridge(s) at the exterior surface of the top wall and/or one or more side walls, for providing grip when e.g. lifting and handling the tray by an operator. The tray is for example a bottle. Side walls provided with ridges or grips are for example the second side wall and the fourth side wall. The screw cap is for example provided with a ridge for providing grip during closing/opening the tray.

In one embodiment, the tray according to the invention comprises side walls, wherein the bottom wall of the bottle has a flat outer surface portion located opposite to the at least one wall of the tray that is at least partly permeable for gases, which at least one wall of the tray that is at least partly permeable for gases is for example the top wall. For example, the tray has the first side wall comprising the opening, wherein the third side wall is located opposite to the first side wall with the opening, and wherein said third side wall has a flat outer portion at the exterior of the tray. Such a flat outer portion of the third side wall of the tray, e.g. a bottle, allows the bottle to stand upright self-supported. In this upright position of the bottle, the opening is at the upper side and accessible for the purpose of providing the bottle with e.g. prepupae, cleaning solution, etc.

In one embodiment, the tray according to the invention comprises side walls, wherein at least one side wall of said tray, for example the first side wall, comprises an openable part for cleaning of the tray and/or for inserting into and/or retrieving out of the tray, any one or more of feed, water, insect feces, insect excrement, insect larvae, alive and dead prepupae, pupae, exuvia, dead or alive adult insects and cocoons thereof. For example, the tray of the invention has the shape of a bottle with at least a flat bottom wall and an opening in a side wall, e.g. the first side wall, said opening having a circular shape with a diameter of between 4 cm and 10 cm such as about 7 cm or 8 cm-11 cm such as about 8.5 cm. The tray of the invention is filled (fillable) with a batch of prepupae through said opening. Furthermore, incubated pupae are transferred (transferrable) out of the tray of the invention through said opening. Subsequently, the tray is cleaned (cleanable) by introducing a cleaning solution into the tray through said opening in the side wall, according to the invention. Therefore, the size and location of the opening in the wall of the tray of the invention are customized in view of the requirements to fill the tray with prepupae, to release incubated pupae from the tray and to clean the tray before a new batch of prepupae is introduced in the same tray, according to the invention. For example, the tray is a bottle or flask provided with a bottle neck with an opening, and for example the opening of such a bottle is located off-center in the side wall comprising the opening, for example near a side of the side wall, wherein the side wall is the first side wall.

In one embodiment, the tray according to the invention comprises walls, wherein the major surface of the bottom wall of the tray has inner dimensions of between 10 cm and 100 cm (width) and between 20 cm and 200 cm (length), and wherein the height of the side walls of the tray is between 3 cm and 40 cm, and typically the height of the side walls of the tray is between 3 cm and 10 cm. For example, the height of the side walls is between 2.3 cm and 9 cm, such as about 2.5 cm or about 4 cm or about 7 cm-9 cm. In one embodiment, the tray according to the invention comprises walls, wherein the major surface of the bottom wall of the tray has inner dimensions of between 10 cm and 100 cm (width) and between 20 cm and 200 cm (length), and wherein the height of the side walls of the tray is between 3 cm and 40 cm, preferably between 20 cm and 60 cm (width), between 40 cm and 100 cm (length), more preferably about 30 cm (width) and about 70 cm (length); and wherein the height of the side walls is preferably between 4 cm and 15 cm, more preferably between 5 cm and 10 cm, most preferably about 7.5 cm or about 8 cm. Also preferred is the tray with these dimensions of the surface of the bottom wall, and side walls with a height of 2 cm-5 cm, such as about 2.5 cm. Side walls of the tray of the invention which have a height that is at least 25% less than the height of side walls of pupae incubation trays currently used in small scale low-tech insect farming, provides a saving in material required for producing the trays of the invention and provides a saving in farming space and/or farming surface required for incubating a certain number of pupae, according to the invention. Typically, for the purpose of incubating pupae at large scale, a layer of about 1.5 cm to 4.5 cm is provided at the inner surface of the bottom wall of the tray of the invention. Typically, for the purpose of incubating pupae at large scale, a layer of 1.8 kg-4 kg, for example about 2.5 kg, is provided at the inner surface of the bottom wall of the tray of the invention. Such a layer of (pre)pupae of about 2 kg-3 kg typically has an average height of 2 cm-4.5 cm, such as about 2.5 cm, in the tray of the invention. Therefore, with the smooth-surfaced side walls of the tray of the invention, and due to the presence of a top wall, the height of the side walls of the tray of the invention is thus as small as between 2.0 cm and 5 cm, or between 2.5 cm and 9 cm, such as about 8 cm, according to the invention, depending on the actual thickness of the layer of prepupae provided in a tray of the invention, as is appreciated by those with skills in the art. For example, with the tray of the invention comprising side walls with the indicated reduced height compared to current trays for incubating prepupae and pupae, a height reduction of the tray results in more efficient use of a room for incubation of pupae, according to the invention. Reducing the height of the side walls of the tray of the invention may for example provide space for more stacked trays of the invention than the number of trays from the current art that can be stacked within the same incubation room for pupae. These two benefits achieved with the use of the trays of the invention contribute to improved production when using the same space and volume of rooms for incubating pupae as would be used for incubating pupae using current low-tech trays.

In one embodiment, the tray according to the invention has an inner volume of between 4 $dm^3$ and 100 $dm^3$, preferably between 6 $dm^3$ and 30 $dm^3$, more preferably between 8 $dm^3$ and 18 $dm^3$ such as about 16 $dm^3$. Preferably, the tray of the invention has a bottom wall with a surface area at the interior side of the tray, of between about 50,000 $cm^2$ and 200.000 $cm^2$, such as about 100,000 $cm^2$, according to the invention. The inventors established that for example applying batches of between 50 and 500 trays of the invention, such as about 100-300 trays for incubating between 1.000 and 100.000 pupae in each of the trays, such as about 4.000 and 20.000 pupae, is sufficient and enough for producing a number of colonies of adult insects, each colony of adult insects having these indicated numbers of insects, provide for an amount of insect-derived products sufficient and enough to run an insect farm profitably, when the tray of the invention has the inner volume and the surface area of the bottom wall of the tray, as indicated here above. Of course, it will be appreciated that when for example the time for incubating insect pupae is between 5 and 23 days, each day of these between 5 and 23 days, a new batch of trays of the invention will be applied for the start of a new pupae incubation cycle, in order to provide for a continuous supply of adult insects, according to the invention. For example, farming black soldier fly implies the start of a new cycle of pupae incubation using the tray of the invention in cycles of between 19 and 22 days, typically about 20 days.

In one embodiment, the tray according to the invention is made of polypropylene and/or the tray is blow molded, thermoformed, rotation molded or 3D printed. According to the invention, a tray for incubating insect prepupae and insect pupae, such as those from black soldier fly, is preferably made of polypropylene by the application of rotation molding. This way, a tray of the invention is provided that has a smooth inner surface and that has rounded corners in the interior of the tray. Such a smooth surface and rounded corners further prevent prepupae from crawling the side walls of the tray of the invention, further contributing to the applicability of trays of the invention with relatively low side walls with a height less than e.g. 10 cm to 40 cm, according to the invention, such as between 3 cm and 9 cm or less such as about 2.5 cm.

In one embodiment, the tray according to the invention comprises walls, wherein the at least one wall of the tray that is at least partly permeable for gases, for example the top wall, is connected to further walls of the tray by welding such that the presence of any one or more of a ridge, a protrusion, a ledge and a recess between said at least one wall of the tray that is at least partly permeable for gases and any further wall, such as the first, second, third and fourth side wall, of the tray encountered by said at least one wall of the tray that is at least partly permeable for gases is omitted. This way, attaching the at least one wall of the tray that is at least partly permeable for gases, for example the top wall, to further walls of the tray by welding, contributes to a smooth inner surface of the tray of the invention. Omitting any ridges, protrusions, ledges and/or recesses at the interior of the tray of the invention not only prevents prepupae from entering any undesired location in the tray, but also contributes to the efficiency of cleaning after a batch of incubated pupae is subsequently discarded from the tray of the invention. That is to say, a smooth inner surface of the tray of the invention prevents prepupae from starting their transformation to pupae at a location different from the bottom surface of the tray, and a smooth inner surface of the tray of the invention improves the ease of cleaning, once the incubation tray has to be prepared for a next cycle of incubating a batch of pupae.

In one embodiment, the tray according to the invention has an inner side having rounded corners at positions where any of the walls encounters any of the other walls of the cage (tray). As said, a smooth inner surface of the tray of the invention, having rounded corners, facilitates easy cleaning of the tray in between two cycles of incubating prepupae and pupae, and contributes to the avoidance of prepupae crawling along the side walls of the tray, according to the invention.

A second aspect of the invention relates to a rack for holding at least one tray of the invention, wherein the rack has at least one side with at least one opening such that at least one side wall of said tray or trays is/are accessible when said tray or trays are held by the rack. Providing a rack of the invention, the rack comprising a number of trays of the invention, such as about three stacks of about 11 trays each, provides for the fast and easy handling of insects from the stage of prepupae up to the stage that adult insects are about to emerge from incubated pupae. Typically, the rack has openings for receiving 10-40 trays, such as stacks of 5×4 or 3×10 trays (horizontal X vertical stacking, respectively). That is to say, a rack comprising an ordered number of equally spaced trays of the invention, positioned in a way that the opening of the trays, located in a side wall of the trays, such as the first side wall, point in the same direction, i.e. in the direction of the operator involved in filling the trays with prepupae, allows for faster processing of the insects and filling of the trays. Operating trays at increased speed not only saves time and resources, though also contributes to the provision of trays comprising colonies of prepupae at a more synchronized stage.

In one embodiment, the rack of the invention comprises sides, wherein the at least one side of said rack with at least one opening has at least separate one or more opening(s) for receiving each of the one or more trays separately, or is an open side of the rack.

In one embodiment, the rack of the invention is designed such that at least the side wall of the tray(s) that comprise(s) an openable part according to the invention is accessible when said tray(s) is/are held by the rack.

In one embodiment, the rack of the invention is provided with a transportation unit, such as an assembly comprising wheels. A preferred rack of the invention is for example a trolley. Other transportation units which are applicable for combining with the rack of the invention are any one of a conveyer belt with the rack positioned thereon, a controllably moveable platform with the rack positioned thereon, a slide arranged to slide the rack. The one having skills in the art will appreciate that yet alternative transportation units are applicable for the purpose, as well. Controllable transportation units are preferred, such as programmable robot platforms comprising slides or wheels.

In one embodiment, the rack of the invention is arranged to hold between two and hundred trays, wherein the distance between two adjacent trays is between 3 cm and 20 cm in the vertical direction. In one embodiment, the rack of the invention is arranged to hold between 15 and 30 trays, such as 24 trays. For example, the distance in the vertical direction between adjacent trays in the rack is 4 cm-15 cm, or 5 cm-12 cm, or 6 cm-10 cm, such as between 7 cm and 9 cm, or about 10 cm.

In one embodiment, the rack of the invention is arranged to hold between two and hundred trays, wherein the distance between two adjacent trays is between 3 cm and 20 cm in the horizontal direction, preferably between 4 cm and 10 cm, more preferably between 5.5 cm and 7.5 cm. In one embodiment, the rack of the invention is arranged to hold preferably between three and fifty trays positioned vertically relative to each other, preferably about 33 trays, wherein the distance between two adjacent trays is preferably about 7.5 cm in the vertical direction. Distances of between 3 cm and 20 cm between adjacent trays in stacks of trays in the rack of the invention, preferably a distance of between 5 cm and 10 cm, allows for compact use of the room in which pupae are incubated, whereas at the same time, trays positioned side by side in stack at these distances, allow for sufficient and efficacious exchange of water vapor, carbon dioxide and ammonia from the inside of the trays to the environment, and for adequate entry of air comprising oxygen into the trays, for providing the incubated prepupae and pupae optimally with the required levels of oxygen beneficial to optimal transformation to adult insects. For example, adjacent trays in the rack are positioned at between about 0.5 cm and 20 cm from each other in the horizontal direction, such as at a distance of about 1 cm and 3 cm. For example, adjacent trays in the rack are positioned at between about 6 cm and 10 cm from each other in the vertical direction, such as at a distance of about 7 cm and 8.5 cm. The top wall is for example the side which is at least partly permeable for gases, and for moisture. Placed in the rack, adjacent trays positioned at a distance of about 10 cm in the vertical direction and about 1 cm in the horizontal direction, allow for optimal exchange of gases and water vapour between the interior of the trays and the surrounding of the rack bearing said trays, when the top wall is the wall of the trays which is at least partly permeable for gases.

A third aspect of the invention relates to an assembly comprising a rack of the invention and at least one tray of the invention.

A fourth aspect of the invention relates to the use of a tray of the invention or relates to the use of the rack of the invention provided with at least one tray of the invention, for incubating insect prepupae and/or insect pupae.

In one embodiment, the use of the tray or use of the rack provided with trays according to the invention, wherein the insect prepupae and/or insect pupae are of black soldier fly.

A fifth aspect of the invention relates to a method for incubating insect prepupae and/or insect pupae, preferably of black soldier fly, comprising the steps of:
providing a rack of the invention comprising at least one tray of the invention, or providing the assembly of the invention;
positioning the rack comprising the one or more trays such that the trays are positioned in upright orientation with the closable opening located at the top side of the upright positioned trays;
loading the trays through said closable opening with between 1.000 and 100.000 insect prepupae, and closing said closable opening;
positioning the rack such that the major surface of the bottom wall of the trays is positioned essentially parallel to the horizontal, herewith providing a layer of the insect prepupae at the major surface of the bottom wall of the trays of between 1.5 cm and 4.0 cm on average;
incubating the assembly of the rack and tray(s) for between 5 days and 23 days.

Preferably, the trays are provided with prepupae, e.g. of black soldier fly, which prepupae are essentially of the same age, such as black soldier fly prepupae differing in age for between 0 to 2 days, such as between 2 hours and 24 hours, according to the invention.

Preferably the layer of the insect prepupae provided at the major surface of the bottom wall of the trays of the invention is about 2.5 cm on average, according to the invention, when the height of the side walls of the tray is typically between 3.5 cm and 8 cm, such as about 5 cm or about 7 cm, or 2.2 cm-2.8 cm, such as about 2.5 cm, or about 8 cm. It has been established that with a layer of prepupae, and subsequently pupae, on the bottom surface of the interior of the tray of the invention, of on average about 2.5 cm, transfer of heat produced by the incubated insects in the colony from said colony to the environment is efficacious and sufficient in order to optimally incubate the pupae. Furthermore, it has also been established that with trays according to the invention, comprising a layer of about 2.5 cm of (pre)pupae, said trays placed in a rack of the invention at distances of about 10 cm (horizontal) and about 1 cm (vertical) from adjacent trays, wherein the height of the side walls (corresponding to the distance between the bottom wall and the top wall of the trays) is about 8 cm, the rate and extent of water evaporation from the (pre)pupae in the trays is such that adult insects efficiently and efficaciously emerge during the incubation period of 17-22 days. The (pre)pupae do not dry out and the (pre)pupae are not wetted, during incubation, therewith preventing hampered development of the adult insects and preventing dying of the pupae and preventing for example growth of mold in/on the pupae due to a moist milieu.

Preferably, the rack of the invention comprising the trays of the invention comprising batches of prepupae allowed to transform to pupae, pupae allowed to transform to adult insects, is incubated for between 17 days and 22 days, more preferably for about 20 days. Preferably, the pupae are pupae of black soldier fly. Preferably, the temperature during the pupae incubation is between 18° C. and 29° C., preferably about 22° C.-26° C., according to the invention.

BRIEF DESCRIPTION OF THE DRAWINGS

FIG. 4. Exploded view of the tray 10 and 100 being a bottle. The screw cap 40 is provided with a protrusion 45 fitting with the bayonet catch 60 located at the bottle neck 11 of the openable part 30. Interior side walls 21', 22' and interior bottom wall 25' are depicted. Top wall 26 connectable with the upper ridge 70 of the four side walls with weld 71.

FIG. 5. Rack 200 for holding at least one tray, comprising apertures 80 for trays 10, 100. The rack 200 has a side 200a with openings 200b such that the first side wall 21 of the tray(s) 10, 100 that comprise(s) an openable part 30 is accessible when said tray(s) is/are held by the rack 200. The rack is typically arranged to hold between two and hundred trays 10, 100, such as 24 trays. The distance d1 between two adjacent trays 10, 100 is typically between 3 cm and 20 cm in the vertical direction, and the distance d2 between two adjacent trays 10, 100 is typically between 3 cm and 20 cm in the horizontal direction.

DEFINITIONS

The term "live" has its regular scientific meaning and here refers to an organism that is in a healthy condition and that has a normal average life expectancy.

The term "air" has its regular scientific meaning and here refers to the air surrounding the earth at ground level.

The term "ambient" has its regular scientific meaning and here refers to that what is surrounding something. Ambient air thus refers to the air surrounding a tray and/or a rack, according to the invention.

The term "insect" has its regular scientific meaning and here refers to all stages of an insect, e.g. pupae, adult insect, neonate larvae, larvae, prepupae.

The term "incubating" has its normal scientific meaning and here incubating refers to the control of conditions external to the prepupae and pupae to ensure successful metamorphosis to the adult form of the insect.

The term "bottle" has its regular scientific meaning and here refers to a rigid or semi-rigid container, or receptacle, with an opening, or mouth, said container or receptacle characteristically having a comparatively narrow neck where the opening or the mouth is found, which opening or mouth can be capped, or closed, with a cap or a closure.

DETAILED DESCRIPTION OF PREFERRED EMBODIMENTS

The following tests were performed with batches of prepupae and pupae of black soldier fly. Typically about 5.000 to 20.000 insects were applied in the tests. Typically, pupae were incubated for about 20 days in the trays. Typically, the prepupae that were introduced in the trays of the following embodiments had an age difference of maximal 2-3 days.

In a preferred embodiment, the tray of the invention is a tray made of polypropylene, provided by rotation molding technique. The tray has side walls with a height of about 6 cm to 9 cm, such as about 7.5 cm. The inner surface of the side walls of the tray, as well as the inner surface of the bottom wall and the top wall is smooth, the top wall being the wall that is at least in part permeable for gases such as air, oxygen, water vapor, ammonia and carbon dioxide, allowing transfer of these gases and transfer of heat from outside the tray inwardly and vice versa. The top wall that is at least partly permeable for gases is a plate provided with essentially circular openings with a diameter of about 3 mm. In a further embodiment, the top wall that is at least partly permeable for gases is a plate provided with essentially squaric openings with sides of about 2.8 mm, the plate made of polypropylene and the openings evenly distributed over the major surface. The plate is glued to the top side of the side walls of the tray. In another embodiment, the top wall is welded to the upper sides of the side walls. In another embodiment, the top wall is a polypropylene mesh with openings formed as hexagons, having an axis about 3.5 mm long, In yet another embodiment, a tray comprises a top wall provided with slits having a short axis of about 2.5 mm, the slits being evenly distributed over the surface area of the top wall. The top wall being made of aluminum or a polymer, e.g. polypropylene. In another embodiment, the tray has smooth side walls with a height of about 7.5 cm, wherein the tray is made of polypropylene. The top wall of this tray is made of polypropylene provided with openings in the shape of ellipses having a minor axis of about 2 mm and a major axis of about 3.5 mm, wherein the top wall is welded to the top side of the side walls of the tray.

These trays were provided with an opening having a circular form with a diameter of between 4 cm and 8 cm, the opening located in a side wall of the tray.

Figure 1:
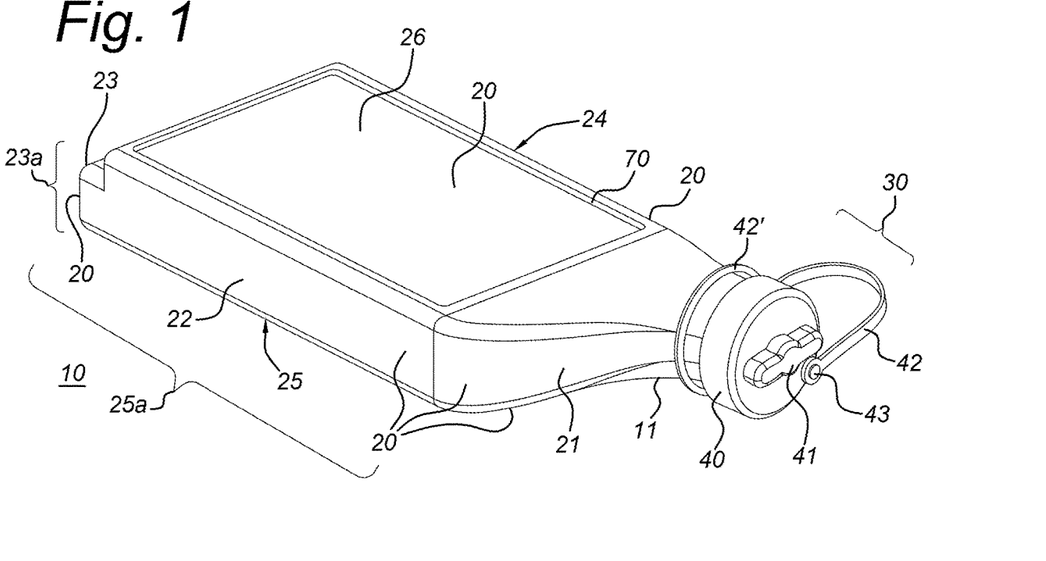
FIG. 1. Tray 10 comprising a space limited by walls 20, wherein said walls comprise a first side wall 21, a second side wall 22, a third side wall 23, a fourth side wall 24, a bottom wall 25 and a top wall 26 and the first side wall 21 comprises an openable part 30, the tray 10 being a bottle and the openable part 30 in the first side wall 21 being a closable opening in the bottle neck 11. The bottom wall 25 has a flat outer surface portion 25*a* located opposite to the top wall 26. The third side wall 23 is located opposite to the first side wall 21 comprising the openable part 30, and said third side wall 23 has a flat outer surface portion 23*a* located opposite to the first side wall 22.

FIG. 1 displays a tray 10 of the invention comprising a space limited by walls 20, wherein said walls comprise a first side wall 21 (front wall, or top wall of the bottle), a second side wall 22, a third side wall 23 (back wall, or bottom wall of the bottle), a fourth side wall 24, a bottom wall 25 and a top wall 26 and the first side wall 21 comprises an openable part 30, the tray 10 being a bottle and the openable part 30 in the first side wall 21 being a closable opening in a bottle neck 11. The bottom wall 25 has a flat outer surface portion 25a located opposite to the top wall 26. The third side wall 23 is located opposite to the first side wall 21 comprising the openable part 30, and said third side wall 23 has a flat outer surface portion 23a located opposite to the first side wall 22. The top wall 26 has a plate comprising openings such that the top wall is at least partly permeable for gases. The plate is connected to the upper side 70 of the first, second, third and fourth side walls 21-24. The tray 10 being a bottle is provided with a cap 40, comprising a ridge 41 for aiding placement of the cap onto the bottle neck 11, covering the opening 30a of the bottle in the first side wall. The cap is connected to the tray through connector 42, at one side 43 attached to the cap and at the opposite side attached to the tray with ring 42' embracing the bottle neck 11.

Figure 2:
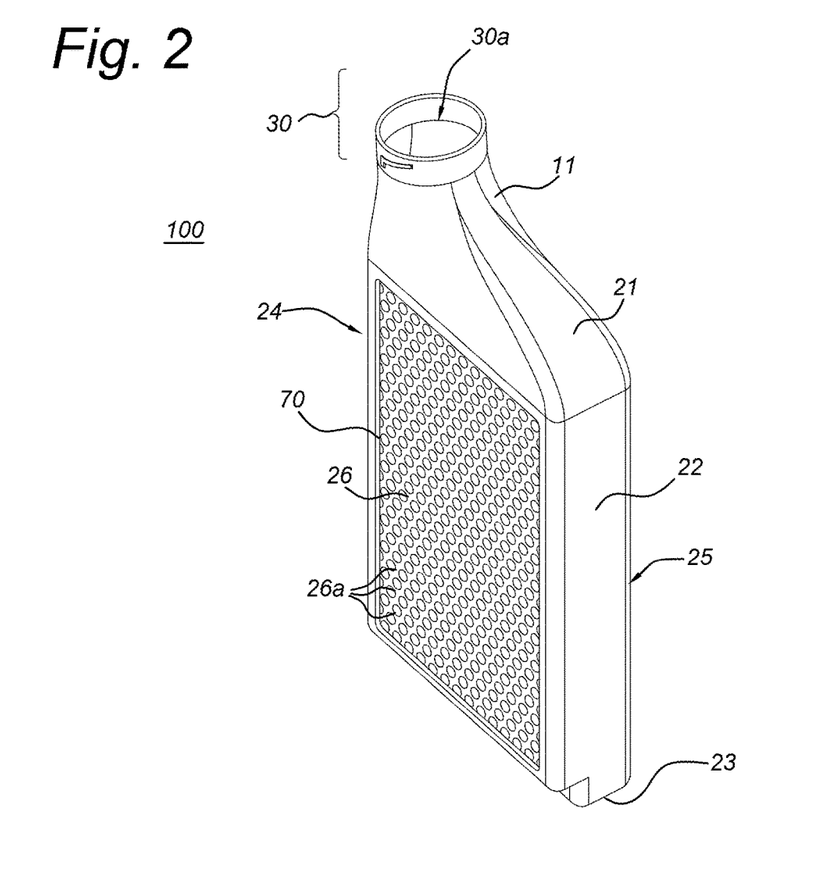
FIG. 2. Tray 100 being a bottle, standing in upright position with the bottle neck 11 comprising the openable part 30, i.e. the opening 30*a* of the bottle, at the top side of the upright positioned tray, in the first side wall. The top wall 26 is at least partly permeable for gases and comprises openings 26*a*.

FIG. 2 displays a tray 100 being a bottle, standing in upright position with the bottle neck 11 comprising the openable part 30, i.e. the opening 30a of the bottle, at the top side of the upright positioned tray, in the first side wall 21. The third side wall 23 is the bottom of the upright bottle, which bottom is a flat surface allowing the bottle to stand upright self-supported on an essentially flat and essentially horizontal surface. The top wall 26 of the tray 100 is at least partly permeable for gases and comprises openings 26a, here squares with sides of about 2.5 mm-3.1 mm.

Figure 3:
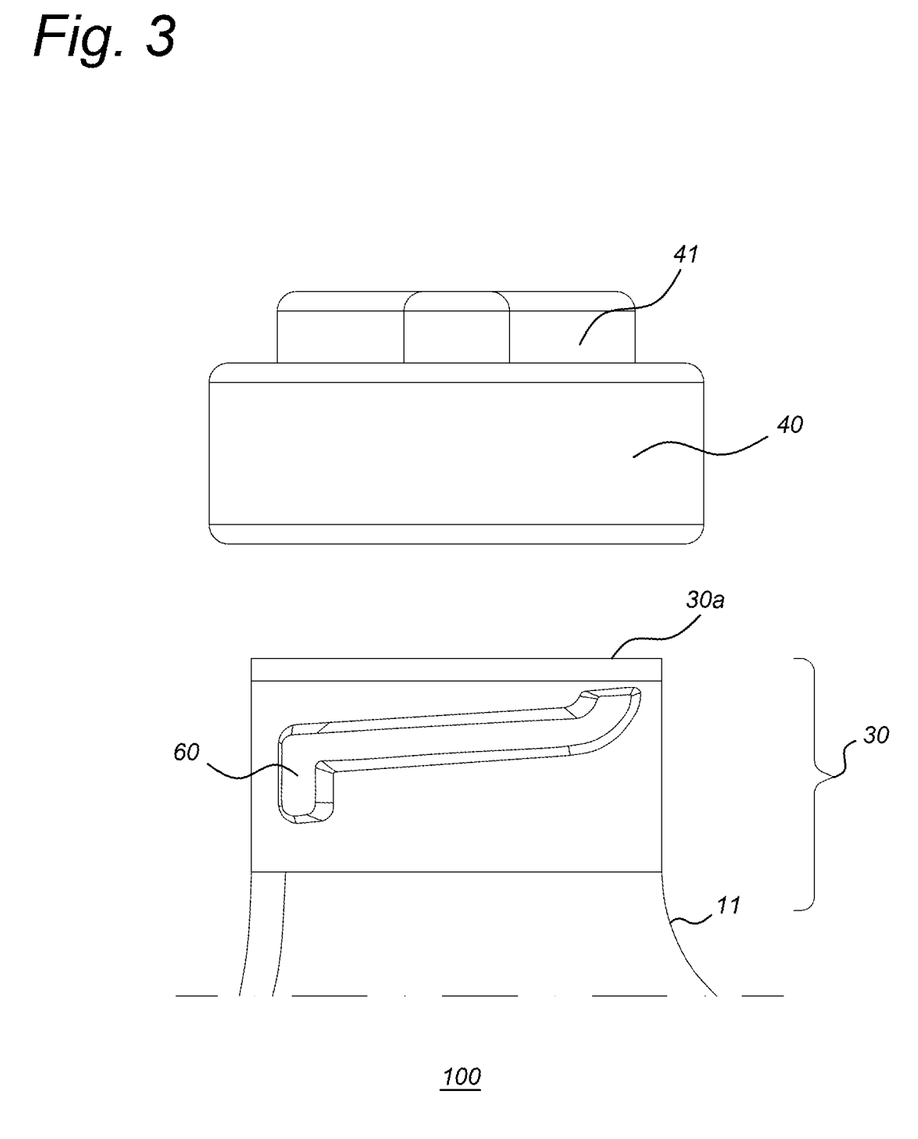
FIG. 3. Part of tray 100 being a bottle, depicting the bottle neck 11, the openable part 30 with opening 30*a*, a bayonet catch 60. Screw cap 40 with grip 41 comprises a protrusion 45 fitting with the bayonet catch.

FIG. 3 shows the blown up part of tray 100 being a bottle, depicting the bottle neck 11, the openable part 30 of the tray with opening 30a, a bayonet catch 60, and a screw cap 40 having an inner diameter fitting with the outer diameter of the openable part 30 of the tray. Screw cap 40 with grip 41 comprises a protrusion 45 fitting with the bayonet catch 60. Positioning the screw cap 40 over the opening 30a of the tray and then screwing the screw cap 40 results in firm fixation of the screw cap 40 on the bottle. The bottle is closed air-tight.

Figure 4:
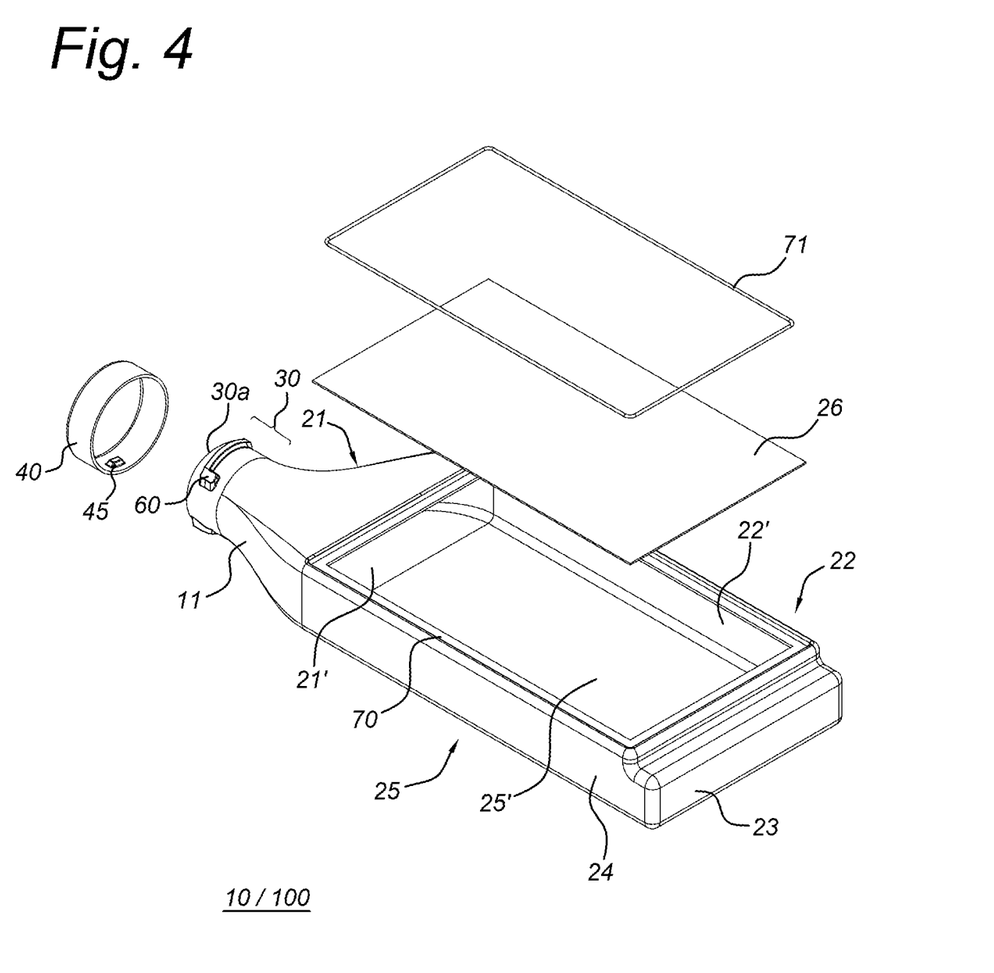

FIG. 4 depicts an exploded view of the tray 10 and 100 being a bottle. The screw cap 40 is provided with a protrusion 45 fitting with the bayonet catch 60 located at the bottle neck 11 of the openable part 30. Interior side walls 21', 22' and interior bottom wall 25', all having a smooth surface, are depicted. Top wall 26 connectable with the upper ridge 70 of the upper part of all four side walls 21-24 of the tray with weld 71.

Figure 5:
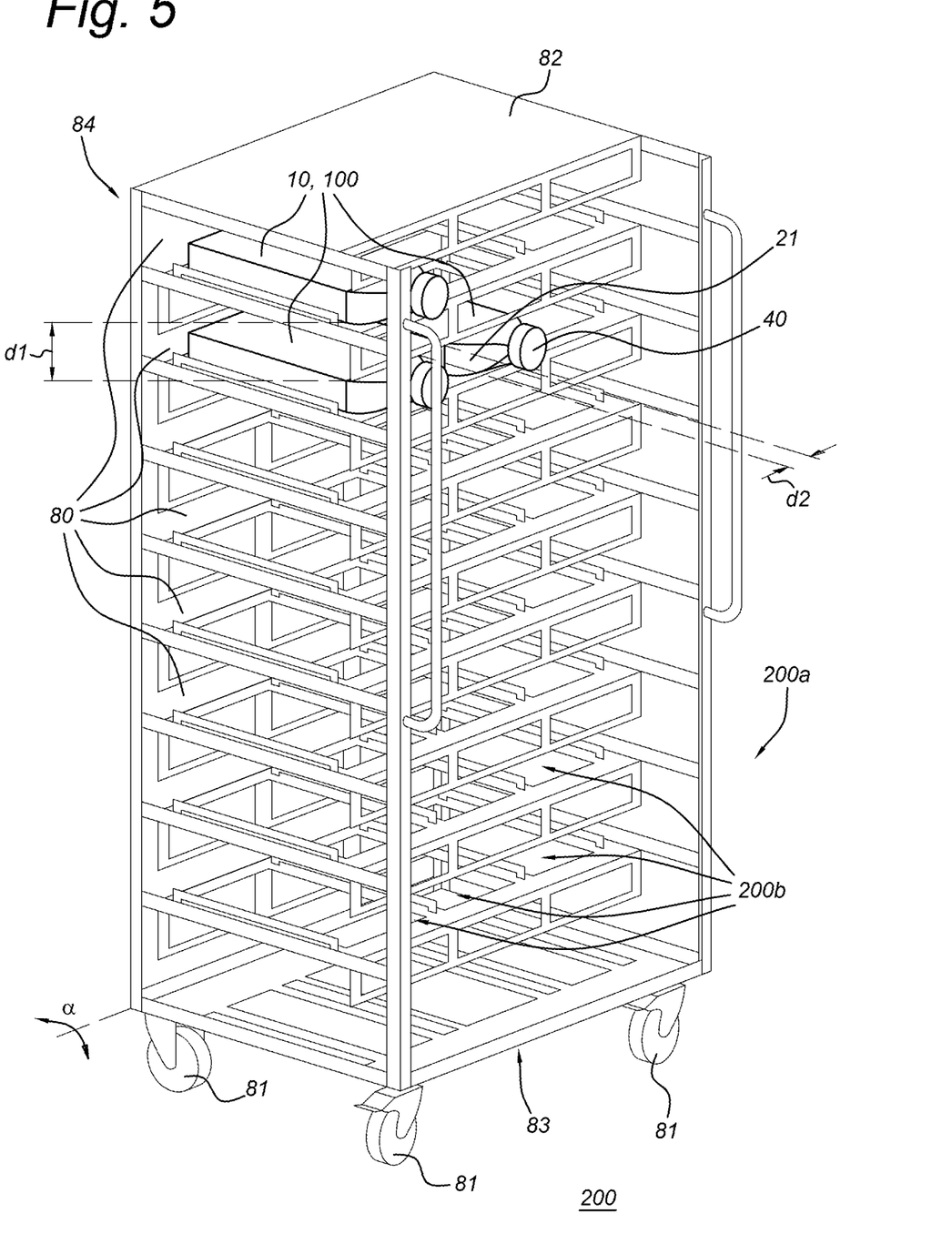

FIG. 5 shows the rack 200 for holding at least one tray, here 3×8 trays (horizontal direction-vertical direction, respectively) comprising apertures 80 for receiving trays 10, 100. The rack 200 has a front side 200a with openings 200b such that the first side wall 21 of the tray(s) 10, 100 that comprise(s) an openable part 30 is accessible when said tray(s) is/are held by the rack 200. The rack is typically arranged to hold between two and hundred trays 10, 100, such as 24 trays. The distance d1 between two adjacent trays 10, 100 is typically between 3 cm and 20 cm in the vertical direction, here about 10 cm, and the distance d2 between two adjacent trays 10, 100 is typically between 0.5 cm and 20 cm in the horizontal direction, such as here about 1 cm. The rack is provided with transportation means, here wheels 81. The rack is rotatable backwardly over an angle α as indicated, such that front side 200a is at the upper side of the rack and the back side 84 is facing the floor.

Figure 6:
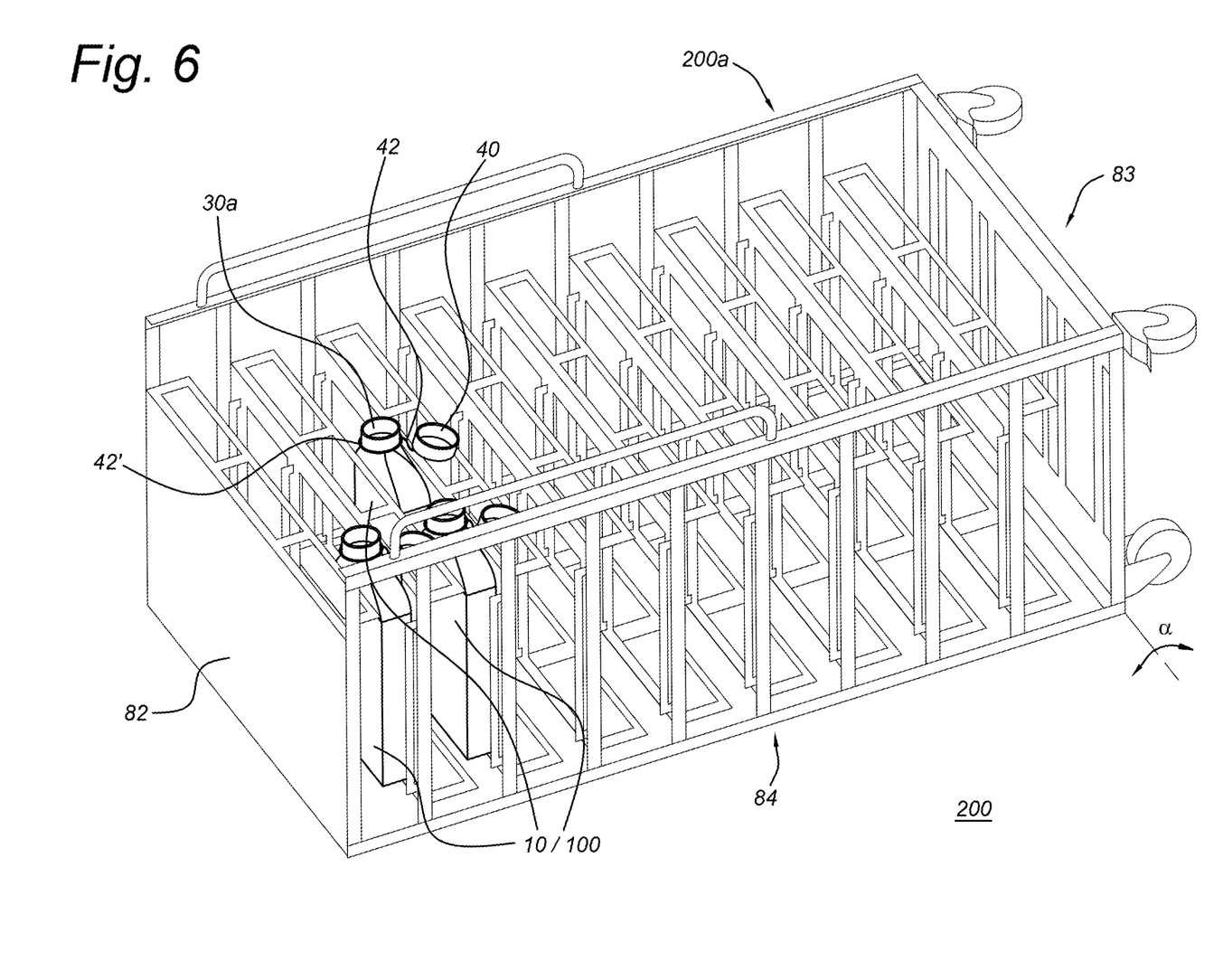
FIG. 6. Rack 200, comprising a tray 10, 100. The rack is positioned such that the tray 10, 100 is standing in upright position with the bottle neck 11 comprising the openable part 30, i.e. the opening 30a of the bottle, at the top side of the upright positioned tray.

FIG. 6 displays the rack 200, comprising trays 10, 100. The rack is positioned such that the trays 10, 100, which are bottles, are oriented in upright position with the bottle neck 11 comprising the openable part 30, i.e. the opening 30a of the bottle, at the upper side of the upright positioned tray. The rack 200 is tilted over an angle α of 90° backwardly such that the front side 200a of the rack now faces upwardly. Bottles are easily accessible this way and are fillable through openings 30a. Screw caps 40 remain attached to the bottles through linkers 42 connected to both the cap and via ring portion 42' to the bottle neck 11 of the bottle. In this orientation, bottom side 83 of the rack and top side 82 of the rack are now pointing sideward.

The trays of these embodiments prevented escape of prepupae from the trays once these prepupae were introduced through the opening of the trays.

Insects inside the trays were not able to penetrate any of the walls of the trays.

Adult insects that emerged from pupae that were incubated at the surface of the bottom wall of the trays were not capable of passing the openings in the top wall of the trays, that was partly permeable for gases.

Subsequent farming of adult insects that emerged from pupae incubated in the trays of the above embodiments, revealed that these adult insects were equally viable and vivid as adult insects retrieved from pupae incubated in high-side walled trays known in the art which are open at the top side of the side walls. That is to say, incubating pupae in the trays according to the invention and in particular in the trays here outlined above, did not hamper proper transformation into adult insects, did not delay the transformation, did not result in more dead insects, nor in insects with e.g. lower body weight.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims.

The invention claimed is:

1. A bottle for incubating insect pupae and/or insect prepupae, comprising:
   a plurality of walls comprising a first side wall, a second side wall, a third side wall, a fourth side wall, a top wall, and a bottom wall opposite the top wall, wherein the plurality of walls defining a space for housing insect prepupae and pupae;
   wherein each of the plurality of walls is impenetrable by an insect;
   wherein the top wall is at least partly permeable for gases, wherein the top wall comprises a plurality of openings selected from a group consisting of: a screen, a mesh, a gauze, a web, a net, a plate with perforations, a sieve, and a filter;
   wherein the plurality of openings each has a form selected from the group consisting of:
      a circular form with a diameter of between 0.7 mm and 3.8 mm,
      an ellipse form with a minor axis with a length of between 0.7 mm and 3.8 mm and with a major axis of between 0.7 mm and 3.8 mm, or
      a slit form having a minor axis of between 0.7 mm and 3.8 mm; and
   wherein one of the first, the second, the third, and the fourth side walls comprises a bottle neck which is openable and closeable, and wherein the others of the first, the second, the third, and the fourth side walls are closed.

2. The bottle according to claim 1, wherein the top wall is made of a material selected from one of: a metal, aluminum, an alloy, stainless steel, a polymer, a polymer blend, a plastic, a blow-molded polymer, a blow-molded polymer blend, a blow-molded plastic, or a combination thereof.

3. The bottle according to claim 1, wherein the surface of the top wall that is at least partly permeable for gases is a smooth surface.

4. The bottle according to claim 1, wherein at least one of the walls of the bottle has a wall thickness of between 1 mm and 12 mm.

5. The bottle according to claim 1, wherein the top wall of the bottle is made of polypropylene, polyethylene, aluminum or stainless steel.

6. The bottle according to claim 1, wherein the top wall of the bottle is a plate provided with the slits, said slits having a minor axis of between 0.7 mm and 3.8 mm, or a screen containing the circular openings having a diameter of between 0.7 mm and 3.8 mm.

7. The bottle according to claim 1, wherein the plurality of openings allow the passage of oxygen, carbon dioxide, and water vapor.

8. The bottle according to claim 1, wherein the plurality of walls of the bottles are impenetrable by adult insects.

9. The bottle according to claim 1, wherein the openable part has a circular cross section with a diameter of between 4 cm and 14 cm or a rectangular cross section with sides of between 4 cm and 14 cm.

10. The tray bottle according to claim 9, wherein the bottom wall of the bottle has a flat outer surface portion that is at least partly permeable for gases.

11. The bottle according to claim 1, wherein the bottle is made of polypropylene and/or wherein the bottle is blow molded, thermoformed, rotation molded, or 3D printed.

12. The bottle according to claim 1, wherein an inner side of the bottle has rounded corners at positions where any of the walls encounter any of the other walls of the bottle.

13. A system comprising:
   at least one bottle according to claim 1,
   a rack for holding the at least one bottle, wherein the rack has at least one side with at least one opening such that at least one side wall of said bottle is accessible when said bottle is held by the rack.

14. The system according to claim 13, wherein the at least one side of said rack with at least one opening comprises:
   one or more separate openings, each separate opening receiving one of the at least one bottle, or
   an open side of the rack receiving at least one of the bottle.

15. The system according to claim 13, wherein the rack is provided with a transportation unit selected from the group consisting of:
   an assembly comprising wheels provided on the rack,
   a conveyer belt with the rack positioned thereon,
   a controllably moveable platform with the rack positioned thereon, or
   a slide arranged to slide the rack.

16. A method for incubating insect prepupae and/or insect pupae comprising the steps of:
   providing a rack comprising one or more bottles according to claim 1 placed thereon, the rack having at least one side with at least one opening such that at least one side wall of the one or more bottles are accessible;
   positioning the rack such that each bottle is positioned in an upright orientation with the closable opening facing upward;
   loading each bottle through said closable opening with between 1,000 and 100,000 insect prepupae and closing said closable opening;
   positioning the rack such that the surface of the bottom wall of each bottle is positioned horizontally such that a layer of the insect prepupae is provided on the surface of the bottom wall of each bottle of between 1.5 cm and 4.0 cm on average; and
   incubating the rack and each bottle for between 5 days and 23 days.

* * * * *